US007479381B1

(12) United States Patent
Kuo et al.

(10) Patent No.: US 7,479,381 B1
(45) Date of Patent: Jan. 20, 2009

(54) **PRODUCTION OF ITACONIC ACID BY *PSEUDOZYMA ANTARCTICA***

(75) Inventors: Tsung Min Kuo, Peoria, IL (US); Cletus P. Kurtzman, Peoria, IL (US); William E. Levinson, Peoria, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 229 days.

(21) Appl. No.: 11/639,762

(22) Filed: Dec. 15, 2006

(51) Int. Cl.
*C12P 7/44* (2006.01)
*C12N 1/00* (2006.01)

(52) U.S. Cl. .................. 435/136; 435/255.1; 435/255.4

(58) Field of Classification Search ........................ None
See application file for complete search history.

(56) References Cited

U.S. PATENT DOCUMENTS

| 3,044,941 A | 7/1962 | Nubel et al. |
| 3,078,217 A | 2/1963 | Balti et al. |
| 5,231,016 A | 7/1993 | Cros et al. |
| 5,273,898 A | 12/1993 | Ishii |
| 5,457,040 A | 10/1995 | Jarry et al. |
| 6,171,831 B1 | 1/2001 | Tsai et al. |

OTHER PUBLICATIONS

Wilke, Th., et al., "Biotechnical Production of Itaconic Acid", Appl. Microbiol. Biotechnol., 2001, 56, pp. 289-295.

*Primary Examiner*—Herbert J. Lilling
(74) *Attorney, Agent, or Firm*—John Fado; Randall E. Deck; Lesley Shaw

(57) ABSTRACT

Itaconic acid may be produced in high yields by fermentation with a yeast, *Pseudozyma antarctica* NRRL Y-30980.

15 Claims, 3 Drawing Sheets

PRODUCTION OF ITACONIC ACID BY *PSEUDOZYMA ANTARCTICA*

BACKGROUND OF THE INVENTION

1. Field of the Invention

The invention relates to a method for producing itaconic acid in high yields by fermentation with a yeast.

2. Description of the Prior Art

Itaconic acid (CAS #: 97-65-4) (methylenebutanedioic acid) is an α-substituted acrylic acid that is used in the manufacture of synthetic resins, coatings, and other industrial products (Tate, BE. Itaconic acid and derivatives. In Kirk-Othmer Encyclopedia of Chemical Technology, edn 3rd. Edited by Grayson M, Eckroth D: John Wiley & Sons; 1981. vol 13; and Willke T and Vorlop K D. Biotechnological production of itaconic acid. Appl Microbiol Biotechnol 2001; 56:289-295). It is produced commercially by the fungal fermentation of carbohydrates. The total market for itaconic acid has been quoted as being between 10,000 to 15,000 metric tons per year worldwide (Willke T, and Vorlop K D. Industrial bioconversion of renewable resources as an alternative to conventional chemistry. Appl Microbiol Biotechnol 2004; 66:131-142) with a price that is ten-times that of citric acid, a more widely used fermentation product (Bressler E and Braun S. Conversion of citric acid to itaconic acid in a novel liquid membrane bioreactor. Journal of Chemical Technology & Biotechnology 2000; 75:66-72).

The organism most often used for itaconic acid production is *Aspergillus terreus*, grown under phosphate-limited conditions (Willke & Vorlop, 2001, ibid; Roehr M and Kubicek C P. Further organic acids. In Biotechnology: Products of primary metabolism, edn 2. Edited by Roehr M: VCH Verlagsgesellschaft mbH; 1996:364-379. [Rehm H-J, Reed G (Series Editor): Biotechnology, vol 6]; and Lockwood L B: Production of organic acids by fermentation. In Microbial Technology, edn 2nd. Edited by Peppler H J, Perlman D: Academic Press; 1979:355-387. vol 1), although some species of the plant pathogenic fungal genus *Ustilago*, a basidiomycete, are also known to produce itaconic acid during fermentation (Willke & Vorlop, 2001, ibid). The sensitivity of *A. terreus* fermentations to metal concentrations (Lockwood, ibid) and difficulties working with filamentous organisms in bioreactors has led to the testing of yeasts for possible itaconic acid production. The patent literature in this area, reviewed by Willke and Vorlop (Willke & Vorlop, 2001, ibid), includes reports of itaconic acid production by a *Candida* mutant strain and *Rhodotorula* species. Tabuchi et al. (Itaconic acid fermentation by a yeast belonging to the genus *Candida*. Agricultural and Biological Chemistry 1981; 45:472-479) isolated a strain, putatively identified as a *Candida*, that produced itaconic acid at a 35% yield when grown under phosphate-limited conditions.

However, despite these advances, the need remains for an improved process for producing itaconic acid.

SUMMARY OF THE INVENTION

We have now discovered that itaconic acid may be produced in high yields by fermentation with a yeast, *Pseudozyma antarctica* NRRL Y-30980. A fermentation medium is inoculated with the strain and incubated under aerobic conditions and for a period of time effective to produce itaconic acid, which acid may be subsequently recovered from the fermentation medium.

In accordance with this discovery, it is an object of this invention to provide a fermentative method for the production of itaconic acid using a yeast rather than a filamentous fungus.

Another object of this invention is to provide a method for the fermentative production of itaconic acid in high yields from a variety of simple sugars as carbon sources.

Other objects and advantages of the invention will become readily apparent from the ensuing description.

DETAILED DESCRIPTION OF THE INVENTION

Figure 1:
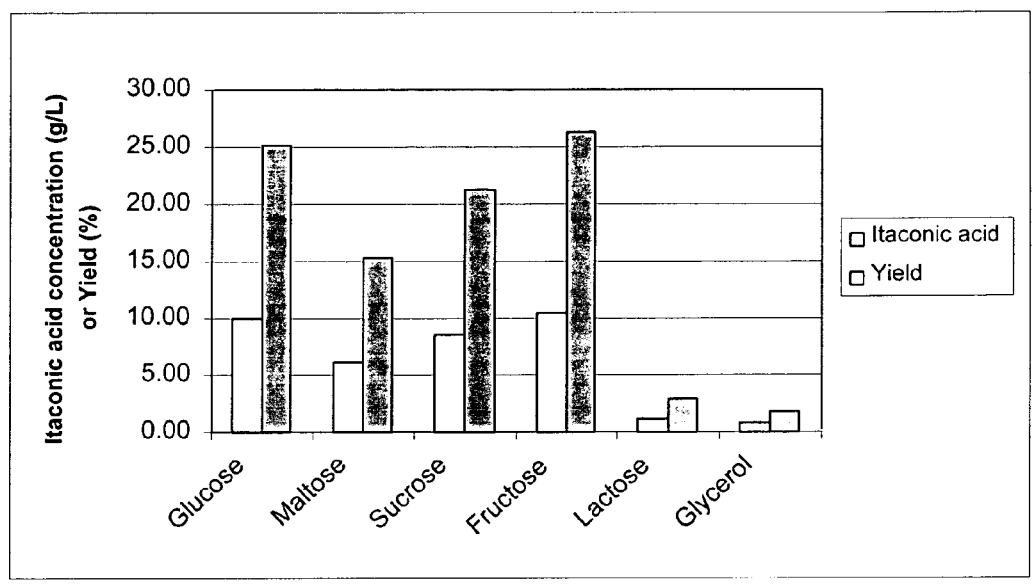
FIG. 1 shows itaconic acid production by *Pseudozyma antarctica* NRRL Y-30980 (previously Y-7808) from various carbon sources as described in Example 1. Data are the average of duplicates. Yield is based on initial concentration of carbon source (40 g/L).

The preferred yeast strain for use herein is a strain of *Pseudozyma antarctica* which has been deposited under the provisions of the Budapest Treaty in the Agricultural Research Service Culture Collection in Peoria, Ill., on Oct. 25, 2006, and has been assigned deposit accession number NRRL Y-30980. This same strain of *Pseudozyma antarctica* was originally described by H. Ito et al. as a strain of *Trichosporon oryzae* isolated in Japan, and was subsequently reclassified as *Candida antarctica* and finally *Pseudozyma antarctica*. The same strain was previously available from the general collection of the Agricultural Research Service Culture Collection under accession number NRRL Y-7808, and was also deposited at other depositories as *Pseudozyma antarctica* deposit accession numbers ATCC 28323 and CBS 6678. Thus, it is understood that this invention may also be practiced using this same strain from any of these other deposit accessions with the same results.

Species of *Pseudozyma* are basidiomycetes and are believed to be closely related to *Ustilago* [Boekhout and Fell: *Pseudozyma* Bandoni emend. Boekhout and a comparison with the yeast state of *Ustilago maydis* (De Candolle) Corda. In The yeasts A taxonomic study. Edited by Kurtzman C P, Fell J W: Elsevier Science Publishers; 1998:790-797, particularly pages 791-792, the contents of which are incorporated by reference herein]. The cultural and biochemical characteristics of *P. antarctica* strain Y-30980 are substantially the same as described in Boekhout and Fell (ibid). The strain is differentiated from other strains based on DNA relatedness and 26S rDNA partial sequences, and possesses a DNA base composition expressed as moles percent G+C of 62% [Kurtzman C P. DNA Relatedness among Species of *Sterigmatomyces* and *Fellomyces*. Int. J. Systematic Bacteriology 1990; 40(1):56-59, the contents of which are incorporated by reference herein]. The morphology of the strain is an asporogenous basidiomycete with no known sexual state, and the strain exhibits optimal growth at 25° C. and produces a thermostable, non-specific lipase. Under anaerobic conditions, the strain does not ferment any of glucose, galactose, sucrose, maltose, lactose, raffinose or trehalose. A variety of carbon sources are assimilated, including glucose, galactose, L-sorbose, sucrose, maltose, cellobiose, trehalose, lactose, raffinose, melezitose, soluble starch, D-xylose, L-arabinose, D-arabinose, D-ribose, L-rhamnose, D-glucosamine, ethanol, glycerol, erythritol (slight), ribitol, D-mannitol, D-glucitol, α-methyl-D-glucoside, D-gluconate, 2-keto-gluconate, 5-keto-gluconate, pyruvate (weak), DL-lactate (weak), and inositol. Inulin, galactitol, salicin, and saccharate are not assimilated. The strain utilizes nitrate, does not form starch and is urease negative.

Production of itaconic acid may be accomplished by culture of the aforementioned *Pseudozyma antarctica* NRRL Y-30980 isolate, using conventional techniques under aerobic conditions that are effective to promote growth and itaconic acid production. The fermentation is preferably conducted as a batch process, with agitation, although it may also be conducted as a fed-batch or continuous process. Any number of well-known liquid or solid culture media may be used, although growth on aqueous liquid media is preferred as the acid is secreted into the media and recovery is simplified. A suitable medium will preferably contain sources of carbohydrate, organic or inorganic nitrogen such as from protein, amino acids, yeast extract, yeast autolysates, nitrates, urea, ammonia or preferably ammonium salts, as well as elements such as potassium, magnesium, calcium, zinc and manganese, preferably as salts, phosphorous such as from phosphates, and other growth stimulating components. By way of example, although prepared commercially available media may be used, such as glucose-yeast extract-peptone water, Trypticase-soy broth, and Potato dextrose broth, use of a defined medium such as described in the Example is preferred. A variety of carbon sources will support growth and production of itaconic acid and are suitable for use herein, and include, but are not limited to, one or more of glucose, hydrolyzed starch, hydrolyzed cellulosic materials containing glucose, corn syrups, beet or sugar cane syrups, molasses, sulfite waste liquor, fructose, sucrose, maltose, nectose, and to a lesser extent, lactose and glycerol. However, glucose and fructose are preferred. The various components should be present in concentrations effective to promote growth of the yeast and itaconic acid production.

Although the yeast will grow and produce itaconic acid during fermentation in a medium wherein the nitrogen is provided in either a limiting or an excess amount, optimal production has been achieved in fermentation medium under nitrogen limiting conditions. As used herein, the term "nitrogen limiting amount" refers to a fermentation medium wherein the assimilable nitrogen source is present in an amount such that the rate of growth and/or biomass yield of the yeast is limited below that required for maximal rate of growth and/or biomass yield (i.e., the nitrogen source is present in an amount below that necessary to support the maximal growth rate and/or biomass yield). The actual "nitrogen limiting amount" may vary with the particular media and may be readily determined by routine experimentation by comparing growth rates of the yeast in media under different concentrations of the nitrogen source. Without being limited thereto, nitrogen limiting conditions are effected by use of media wherein the carbohydrate and nitrogen sources are present in amounts such that the C/N ratio is greater than about 80, preferably greater than about 100, and most preferably between about 100 and about 750 (wherein the C/N ratio is measured as the molar ratio of elemental carbon to elemental nitrogen in the respective carbohydrate and nitrogen sources). Optimal rates of itaconic acid production have been effected using media wherein the C/N ratio is about 115 to 116, while optimal yields of itaconic acid production have been effected using media wherein the C/N ratio is about 175 to about 350. Suitable actual concentrations of the nitrogen source will of course vary with the amount of carbon source. By way of example, in a medium containing approximately 80 g/L glucose as the carbon source, the nitrogen concentration may vary between about 3 and about 35 mM, and preferably vary between about 10 and 30 mM (measured as the amount of elemental nitrogen). The medium and fermentation vessel my be optionally sterilized prior to incubation to prevent contamination.

The temperature and pH of the fermentation are not critical, although it is understood that they should be suitable for growth of the yeast. The disclosed *P. antarctica* strain will grow and produce itaconic acid over wide pH and temperature ranges, generally a temperature between about 20 to 37° C., preferably between about 25 to 30° C., and a pH between about 3 to 7, preferably about 5. Neutralization of the acid produced during the fermentation is optional but preferred. For example, the pH of the medium at the commencement of the fermentation is preferably in the range of about 6, and is controlled by addition of base to a pH of about 5 as the fermentation progresses. Control or maintenance of the pH in the course of the fermentation may be accomplished using manual or automatic techniques conventional in the art, such as using automatic pH controllers for adding base. Preferred bases employed for pH control include but are not limited to NaOH and KOH.

Under these cultivation conditions, optimal production of itaconic acid is achieved between about 144 to about 168 hours, after which time acid production decreases gradually. Upon completion of the fermentation, preferably after about 7 to 8 days, the itaconic acid may be isolated or separated from the yeast cells using techniques conventional in the art, such as by centrifugation or filtration.

At the completion of the fermentation, accumulated itaconic acid may be recovered from the fermentation broth using conventional techniques. Although formulations of the itaconic acid may be prepared directly from liquid culture medium from which cells have been removed in the above-described manner, as a practical matter, it is envisioned that commercial formulations of the itaconic acid will require concentration and preferably substantial purification. Purification is particularly preferred for applications demanding a high degree of purity where contamination by enzymes, microbial products, or culture media components may be undesirable.

Without being limited thereto, suitable recovery techniques are described by Willke T and Vorlop K D. (2001, ibid), L. B. Lockwood (Production of Organic Acids by Fermentation, In: Microbial Technology, second edition, vol. 1, ed. by H. J. Peppler et al., Academic Press, 1979, pp. 367-373), Milsom and Meers (Gluconic and Itaconic acids. Comp. Biotechnol.; 1985. 3:681-700), Kobayashi (Japanese Patent 3 621 053, 1971), Kobayashi et al. (Process design for itaconic acid fermentation. Proc. IV IFS: Ferm. Technol. Today. 1972; 215-221), Kobayashi et al. (Japanese Patent 48 092 584, 1973), Kobayashi et al. (Japanese Patent 51 028 711, 1980), and Furuya et al. (Japanese Patent 43 020 706, 1968), the contents of each of which are incorporated by reference herein. The particular recovery step selected will be contingent upon the culture medium used and the desired degree of purity of the itaconic acid. Preferred concentration and purification techniques include, but are not limited to, evaporation, ultrafiltration, reverse osmosis, dialysis and electrodialysis, solvent extraction (including, but not limited to, ether, petroleum ethers, hexane, alkyl acetates, and preferably ethyl acetate), cooling and crystallization of an acidic concentrate, ion-exchange chromatography, particularly using an anion exchange resin with subsequent elution with an aqueous base, treatment of a hot concentrate with activated carbon, followed by filtration, cooling, crystallization, and treatment of the mother liquor from the crystallization by solvent extraction or an anion exchange resin, recrystallization from water when using glucose or sucrose substrates, precipitation of insoluble itaconic acid salts which may then be redissolved by addition of alkali salts such as ammonia, and clarification of the fermentation medium by addition of an alcohol such as methanol followed by filtration and evaporation. However, in a particularly preferred embodiment the itaconic acid may be recovered and purified by evaporation of an acidic fermentation medium supernatant or filtrate, followed by cooling and crystallization, or by solvent extraction such as by acidification of the fermentation medium supernatant or filtrate, followed by extraction with ethyl acetate or other suitable solvent, or by precipitation of insoluble itaconic acid salts. Using these techniques, itaconic acid may be recovered in pure or substantially pure form.

The itaconic acid produced herein may be employed in a wide variety of well-known uses. Examples of potential uses include the preparation of derivatives used in the commodity and specialty markets, and as a specialty comonomer in resins and copolymers. For example, without being limited thereto, as described by Werpy et al. (Top Value Added Chemicals From Biomass. Vol. 1: Results of Screening for Potential Candidates from Sugars and Synthesis Gas. U.S. Department of Energy Office of Scientific and Technical Information, Oak Ridge, Tenn.; 2004. pp. 42-44) and Willke T and Vorlop K D. (2001, ibid), (the contents of each of which are incorporated by reference herein), itaconic acid may be converted to any one of 3- or 4-methyl-GBL, 3-methyl THF, 2-methyl-1,4-BDO, 3- or 4-methyl NMP, 3-methylpyrrolidine, itaconic diamide or 2-methyl-1,4-butanediamine, or it may be used to produce a copolymer with acrylic acid, styrene-butadienes, polyacrylonitriles, to produce polymerized methyl, ethyl or vinyl esters of itaconic acid, or added to vinylidene chloride coatings or organosiloxanes.

The following examples are intended only to further illustrate the invention and are not intended to limit the scope of the subject matter which is defined by the claims.

EXAMPLE 1

Materials and Methods

Yeast strains screened were from the ARS Culture Collection (NRRL), National Center for Agricultural Utilization Research, Peoria, Ill., and were maintained on potato-dextrose-agar slants throughout this study. Itaconic acid (99+%) and thiamine hydrochloride were purchased from Sigma-Aldrich (St. Louis, Mo.). Trypticase-soy broth (TSB), dextrose (glucose), and yeast extract were products of Becton, Dickinson and Co. (Sparks, Md.). Other medium components were laboratory grade or better and used without purification.

Initial screening for organic acid production under nitrogen limited growth conditions was carried out in a medium with the following composition (g/L): Glucose or glycerol, 80; $(NH_4)_2SO_4$, 0.5; $KH_2PO_4$, 1.7; $Na_2HPO_4$, 12; $MgSO_4.7H_2O$, 1.4; $CaCl_2$, 0.02; $ZnSO_4.7H_2O$, 0.02; $FeSO_4.7H_2O$, 0.05; $MnSO_4.H_2O$, 0.02; thiamine hydrochloride, 0.006; yeast extract, 0.5. Initial pH was 6.0 and sterile bromocresol purple (32 mg/L) was added post-autoclave as a pH indicator. After initial screening, the following modifications were made to the medium for itaconic acid production test experiments: $MgSO_4.7H_2O$, 2.5 g/L; $ZnSO_4.7H_2O$, 1.5 µg/L; $MnSO_4.H_2O$, 0.9 µg/L. Other medium modifications made during these experiments are noted below.

The medium was inoculated (1%) from 48-hour cultures grown on TSB. Initial screening was done in 50 mL Erlenmeyer flasks containing 15 mL medium. Itaconic acid production experiments were either 25 or 50 mL volumes in 125-mL flasks. Growth conditions were 28° C. and 200 rpm. During growth, a pH indicator was used to maintain the pH within a desired range by daily additions of 2 M KOH. Growth in the screening experiment was continued until all flasks stopped requiring base addition (day 11). Using pH change as a guide, itaconic acid production experiments were incubated for ten days. Initial screening was done in single cultures, while itaconic acid production studies were performed in duplicate.

A fermentation experiment was performed in an Applikon fermentor controlled by an ADI 1030 Biocontroller equipped with sensors for monitoring temperature, pH, and dissolved oxygen, and monitored with BioXpert software (Applikon, Inc., Foster City, Calif.). The 2 L dished-bottom reactor contained 1 L of medium. Air was supplied at 1 vvm with agitation provided by two marine impellers at 1000 rpm. Temperature was maintained at 28° C. The fermentor was equilibrated at these conditions for 1 hour prior to inoculation and the oxygen concentration was set to a nominal 100% by calibrating the oxygen probe. After equilibration, the medium was inoculated with 10 mL (1%) of a 24-hr-old TSB culture. Initial pH of the medium was 6.0 and was allowed to drop to 5.0 where it was held steady by the addition of 2 M KOH. Antifoam SO-25 (Sigma-Aldrich, St. Louis, Mo.) was added as needed. Duplicate samples were taken at each time point.

Analysis of culture supernatants for organic acids was performed by HPLC with a Phenomenex Synergi Fusion-RP column (150×4.6 mm, 4 µm particle size). The mobile-phase was 0.25% acetic acid (isocratic) and detection was at 201 nm with a diode-array detector. Culture supernatants from the screening experiment that exhibited possible organic acid production were acidified and extracted with ethyl acetate. The extracts were methylated with diazomethane and analyzed by GC-MS.

Sugar concentrations were assayed by the anthrone/sulfuric acid method. Samples were diluted in 50 mM sodium bicarbonate buffer. One volume sample was placed in vials and cooled to 4° C. prior to addition of 2.5 volumes of the anthrone reagent (2 g/L anthrone in concentrated sulfuric acid). The vials were sealed, mixed, and heated to 95° C. for 15 minutes. After cooling, readings were taken at 625 nm.

Results and Discussion

Fourteen yeast strains that had not previously been characterized for organic acid production, including 8 from the genus *Pseudozyma*, were screened for organic acid biosynthesis using the nitrogen-limited screening medium described (C/N ratio=352) (Table 1). Most of the strains tested did not grow well or did not produce significant amounts of acids when grown on glycerol. However, when the strains were grown on glucose, *Pseudozyma antarctica* NRRL Y-30980 (i.e., Y-7808) was found to require the most base addition in order to maintain the pH of the culture (data not shown). Its culture supernatant showed the production of a substantial amount of an unknown compound when analyzed by HPLC. This strain was selected for further work. A second *P. antarctica* strain (NRRL Y-8295) did not exhibit significant acid production from glucose. Mass spectral analysis of the screening culture extract of *P. antarctica* NRRL Y-30980 revealed the major compound to be itaconic acid as identified by a mass spectral library. The HPLC retention time of authentic itaconic acid was the same as the culture product.

The initial screening medium was modified by dropping the concentrations of $FeSO_4$, $ZnSO_4$ and $MnSO_4$ to 0.005 mM for all from 0.18, 0.07 and 0.12 mM, respectively. This new medium was used as a base to test for the effects of magnesium, iron, calcium, and nitrogen concentration on the yield of itaconic acid in flask experiments. No effect on itaconic acid yield was seen at magnesium concentrations of 10 and 20 mM or iron concentrations between 0.01 and 1 mM, either with or without $CaCl_2$ at 0.2 mM. All cultures, including those grown on the initial screening medium, produced approximately 30 g/L itaconic acid from 80 g/L glucose in the starting medium (data not shown), a 37.5% yield. This yield is similar to that seen by Tabuchi et al. for a *Candida* strain grown under phosphate-limited conditions (Tabuchi T et al. 1981, ibid).

The ability of *P. antarctica* to utilize glycerol and sugars other than glucose to produce itaconic acid was also tested (FIG. 1). In this experiment, the carbon source concentration was 40 g/L in the medium and the nitrogen concentration was adjusted to maintain the C/N ratio used in the previous experiment. The monosaccharides glucose and fructose were utilized most efficiently, followed by the disaccharides sucrose and maltose. Lactose and glycerol were the poorest substrates, although both did yield slight amounts of itaconic acid (FIG. 1).

Figure 2:
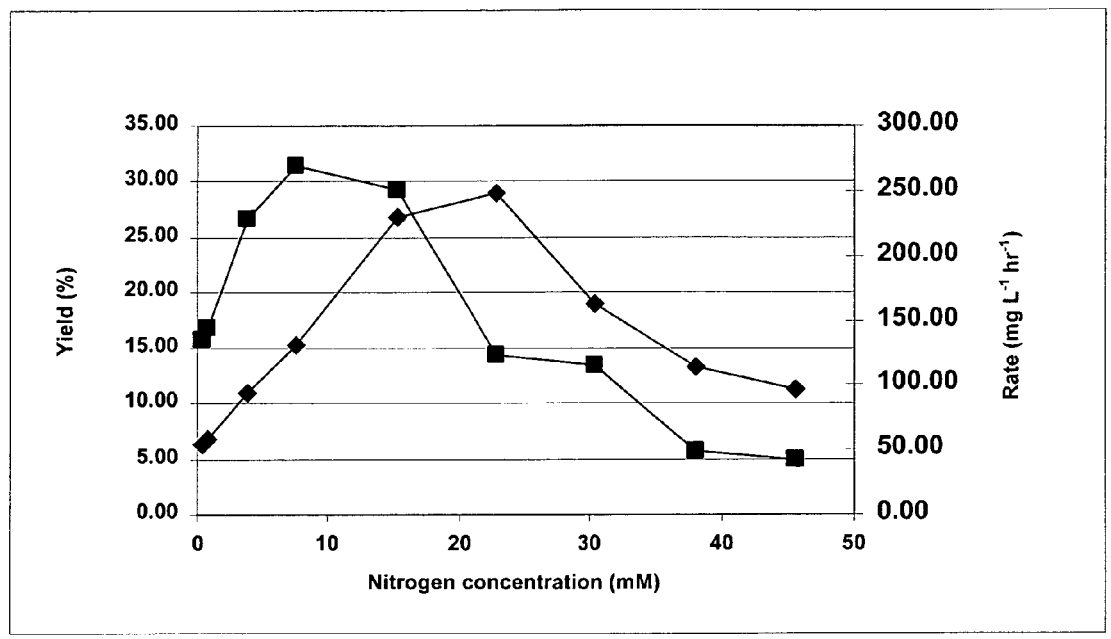
FIG. 2 shows the initial volumetric production rate and yield of itaconic acid versus nitrogen concentration by *Pseudozyma antarctica* NRRL Y-30980 (i.e., Y-7808) in example 1. Diamond, rate; square, yield. Data are the average of duplicates. Yield is based on the initial glucose concentration (80 g/L).
Figure 3:
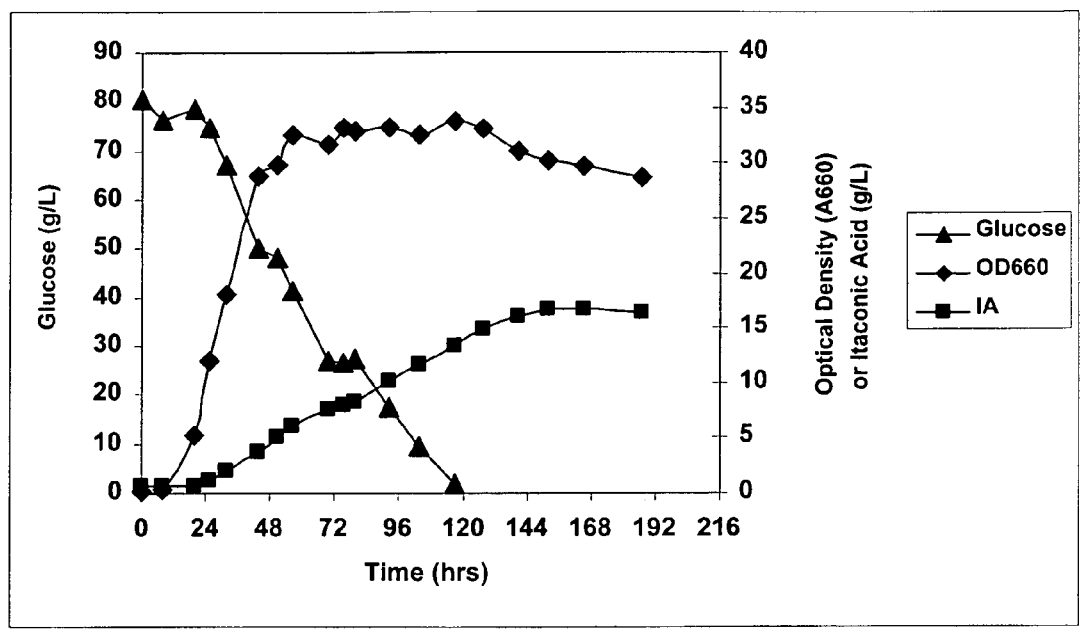
FIG. 3 shows itaconic acid production by *Pseudozyma antarctica* Y-30980 (i.e., Y-7808) in a fermentor with controlled pH in Example 1. All data points are the average of duplicate samples.

In experiments to determine the optimal nitrogen concentration, the magnesium and iron concentrations were set at 10 and 0.2 mM, respectively. Calcium chloride was omitted from the medium. Nitrogen concentrations between 0.038 and 45.6 mM [0.019-22.8 mM $(NH_4)_2SO_4$] were tested for initial rate and yield (FIG. 2). Data showing the amounts of elemental nitrogen and the relative amounts of carbon to nitrogen and their effect on itaconic acid production rate and yield are shown in Table 2. The initial rate was measured after the cultures started to produce itaconic acid, which was dependent on the initial nitrogen concentration (less nitrogen resulted in earlier induction of itaconic acid production). The initial volumetric production rate peaked at 248 mg $L^{-1}$ $hr^{-1}$ with 22.8 mM nitrogen while the best yield (31%) was seen at 7.6 mM nitrogen. The best combination of rate and yield was achieved at 15.2 mM nitrogen with a rate of 230 mg $L^{-1}$ $hr^{-1}$ and a yield of approximately 29%. The yield derived in this experiment was lower than that seen in the previous experiment (for the same medium conditions). The reason for this variability is not known.

Due to the variable nature of the pH control in flask experiments, a fermentor-based experiment with direct pH control was undertaken. Aeration was provided by 1 vvm sparger air and 1000 rpm agitation. These aeration conditions were nominally set as 100% oxygen prior to inoculation. After inoculation, the dissolved oxygen dropped to approximately 85% for a short period towards the beginning of the exponential growth phase (at ~20 hr) and thereafter, rose slowly back to approximately 100%, where it remained for the balance of the fermentation, except for a brief interruption of aeration at approximately 72 hr. The starting pH of the medium was 6.0 and fell with culture growth, reaching 5.0 at approximately 20 hr of incubation time, and was held constant at that level for the rest of the fermentation.

There was an approximately 24-hr lag time prior to the start of itaconic acid production, after which production proceeded at a linear rate of 132 mg $L^{-1}hr^{-1}$ until reaching a maximum concentration of 16.7 g/L at 152 hr (or 6.3 days). This resulted in a yield of 20.9% or about 5 to 10% below that derived from flask studies. The rate of production was below the 230 mg $L^{-1}hr^{-1}$ seen for the same medium composition in flask culture. The overall volumetric production rate, from inoculation to the point of maximum concentration was 110 mg $L^{-1}hr^{-1}$. These yields and volumetric production rates were below the numbers quoted by Willke and Vorlop (2001, ibid) as the maximum achieved in the *A. terreus* process, which has exhibited up to a ~47% yield and 1 g $L^{-1}$ $hr^{-1}$ production rate.

For large-scale production of itaconic acid it is envisioned that the 24-hour lag time prior to the beginning of production would likely be reduced by using a larger volume of inoculating culture. In this case, a 1% inoculation was used to reduce the addition of nutrients from the rich-medium used for the seed-culture. Utilization of a two-stage seed-culture protocol, with the second culture in the production medium, would remove this limitation.

SUMMARY

Itaconic acid is commonly produced by *A. terreus* under phosphate-limited growth conditions. This type of growth-limitation was also used by Tabuchi et al. in a study of itaconic acid production in a strain of *Candida* (Tabuchi T et al. 1981, ibid). Citric acid production in yeast strains, however, may be carried out under nitrogen-limited growth conditions (Anastassiadis S et al. Citric acid production by *Candida* strains under intracellular nitrogen limitation. Appl Microbiol Biotechnol 2002; 60:81-87 and Roehr M et al.: Citric acid. In Biotechnology: Products of primary metabolism, edn 2. Edited by Roehr M: VCH Verlagsgesellschaft mbH; 1996: 307-345. [Rehm H-J, Reed G (Series Editor): Biotechnology, vol 6.]) and this work shows that nitrogen-limitation is able to induce itaconic acid production in high yields by *P. antarctica* NRRL Y-30980 (i.e., Y-7808). It is noteworthy that other *Pseudozyma* strains tested, including a second strain of *P. antarctica*, did not produce itaconic acid. Therefore the ability to produce itaconic acid is a special property of *P. antarctica* NRRL Y-30980 and is not a common trait of the genus.

TABLE 1

Strains screened for organic acid production.

| NRRL Accession # | Species |
| --- | --- |
| YB-4297 | *Aciculoconidium aculeatum* |
| YB-4298 | *Aciculoconidium aculeatum* |
| YB-2364 | *Candida bentonensis* |
| Y-5579 | *Candida hispaniensis* |
| Y-5580 | *Candida hispaniensis* |
| Y-30980* | *Pseudozyma antarctica* |
| Y-8295 | *Pseudozyma antarctica* |
| Y-7954 | *Pseudozyma aphidis* |
| Y-17627 | *Pseudozyma flocculosa* |
| Y-17173 | *Pseudozyma fusiformata* |
| Y-27503 | *Pseudozyma prolifica* |
| Y-17626 | *Pseudozyma rugulosa* |
| Y-7792 | *Pseudozyma tsukubaensis* |
| Y-1095 | *Yarrowia lipolytica* |

*Pseudozyma antarctica* Y-30980 was originally obtained as deposit accession number Y-7808.

TABLE 2

Rate and yield of itaconic acid production versus carbon/nitrogen ratio (initial glucose concentration was 80 g/L [443.95 mM])

| Nitrogen (mM) | Glucose/N molar ratio | Carbon/N molar ratio | Rate (mg/L*hr) | Yield (%) |
|---|---|---|---|---|
| 0.38 | 1168.3 | 7009.7 | 53.9 | 15.7 |
| 0.76 | 584.1 | 3504.9 | 57.8 | 16.8 |
| 3.8 | 116.8 | 701.0 | 93.5 | 26.7 |
| 7.6 | 58.4 | 350.5 | 131.0 | 31.4 |
| 15.2 | 29.2 | 175.2 | 230.2 | 29.3 |
| 22.8 | 19.5 | 116.8 | 248.2 | 14.4 |
| 30.4 | 14.6 | 87.6 | 161.9 | 13.4 |
| 38.0 | 11.7 | 70.1 | 113.7 | 5.7 |
| 45.6 | 9.7 | 58.4 | 96.3 | 4.9 |

It is understood that the foregoing detailed description is given merely by way of illustration and that modifications and variations may be made therein without departing from the spirit and scope of the invention.

We claim:

1. A method for producing itaconic acid or salts thereof comprising:
   a. inoculating a fermentation medium with *Pseudozyma antarctica* NRRL Y-30980 and incubating under aerobic conditions and for a period of time effective to produce itaconic acid in said medium, and
   b. recovering said itaconic acid from said fermentation medium.

2. The method of claim 1 wherein said recovering comprises separating cells of said *Pseudozyma* from said fermentation medium and concentrating said itaconic acid in said fermentation medium.

3. The method of claim 1 wherein said itaconic acid is recovered in substantially pure form and said recovering comprises separating cells of said *Pseudozyma* from said fermentation medium and at least partially purifying said itaconic acid from said fermentation medium.

4. The method of claim 3 wherein said itaconic acid is at least partially purified by solvent extraction or precipitation of insoluble itaconic acid salts.

5. The method of claim 1 wherein said fermentation medium comprises a carbohydrate effective to support growth of said *Pseudozyma*.

6. The method of claim 5 wherein said carbohydrate comprises glucose, fructose, sucrose, maltose, nectose, glycerol, molasses, hydrolyzed starch, hydrolyzed cellulosic material comprising glucose, corn syrup, beet syrup, sugar cane syrup, sulfite waste liquor, lactose or combinations thereof.

7. The method of claim 6 wherein said carbohydrate comprises glucose, fructose, hydrolyzed starch, hydrolyzed cellulosic material comprising glucose, or combinations thereof.

8. The method of claim 5 wherein said fermentation medium comprises a nitrogen source present in a nitrogen limiting amount.

9. The method of claim 8 wherein said medium comprises a carbon to nitrogen ratio of greater than about 80.

10. The method of claim 8 wherein said medium comprises a carbon to nitrogen ratio of greater than about 100.

11. The method of claim 8 wherein said medium comprises a carbon to nitrogen ratio between about 100 and about 750.

12. The method of claim 8 wherein said medium comprises a carbon to nitrogen ratio between about 100 and about 350.

13. The method of claim 8 wherein said medium comprises a carbon to nitrogen ratio between about 175 and about 350.

14. The method of claim 1 wherein said incubating is at a temperature between about 20 to about 37° C.

15. The method of claim 1 wherein said incubating is at a temperature between about 25 to about 30° C.

* * * * *